United States Patent [19]

Brous et al.

[11] 4,388,184

[45] Jun. 14, 1983

[54] PRESSURE AND FLUID FLOW ACTIVATED, SIMPLIFIED PROPORTIONING SYSTEM

[76] Inventors: Donald Brous, 110 Hunt Rd., Peterborough, N.H. 03458; Robert H. Cox, 33 Ferncliff Rd., Scarsdale, N.Y. 10583

[21] Appl. No.: 418,046

[22] Filed: Sep. 14, 1982

Related U.S. Application Data

[63] Continuation-in-part of Ser. No. 161,065, Jun. 19, 1980, abandoned.

[51] Int. Cl.³ .............................................. B01D 31/00
[52] U.S. Cl. .................................. 210/96.2; 210/101; 210/105; 210/134; 210/137; 210/321.3
[58] Field of Search ...................... 210/96.2, 101, 103, 210/137, 321.1–321.5, 90, 96.1, 105, 130, 134, 416.1; 137/93, 99

[56] References Cited

U.S. PATENT DOCUMENTS

| | | | |
|---|---|---|---|
| 3,352,779 | 11/1967 | Austin et al. | 210/103 |
| 3,605,783 | 9/1971 | Pecker et al. | 210/96.2 X |
| 3,774,762 | 11/1973 | Lichtenstein | 210/94 |
| 3,814,249 | 6/1974 | Eaton | 210/86 |
| 4,060,485 | 11/1977 | Eaton | 210/87 |
| 4,096,059 | 6/1978 | Pinkerton | 137/99 X |
| 4,136,708 | 1/1979 | Cosentino et al. | 137/99 |

Primary Examiner—David R. Sadowski
Attorney, Agent, or Firm—Charles R. Fay

[57] ABSTRACT

Continuously operating batch system for proportioning concentrate for blood treatment through the use of a proportioning tank and means for filling and emptying the same dependent upon pressure and flow in the mixing tank.

11 Claims, 2 Drawing Figures

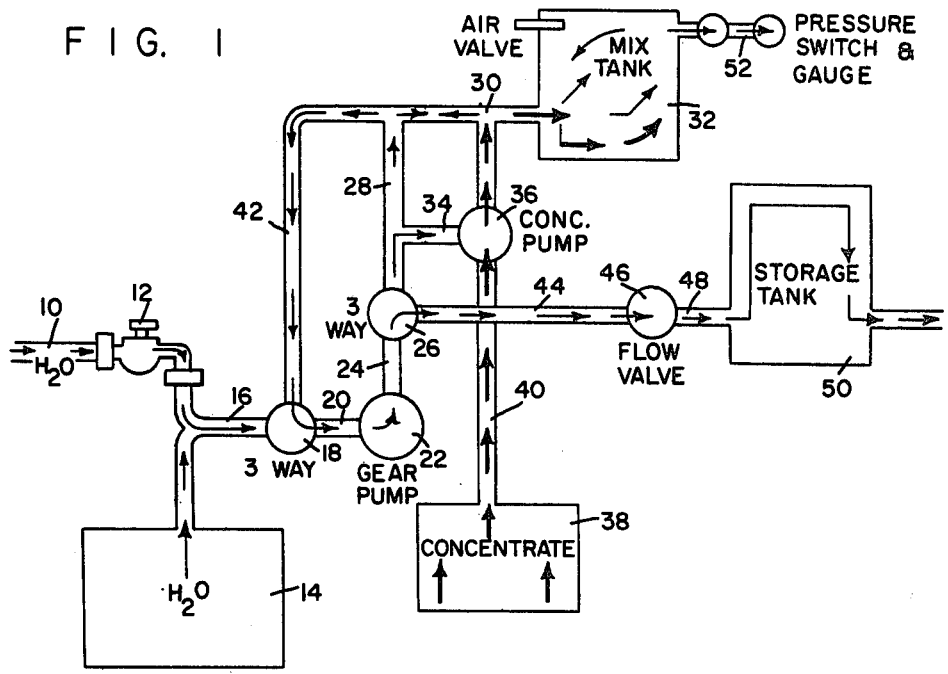
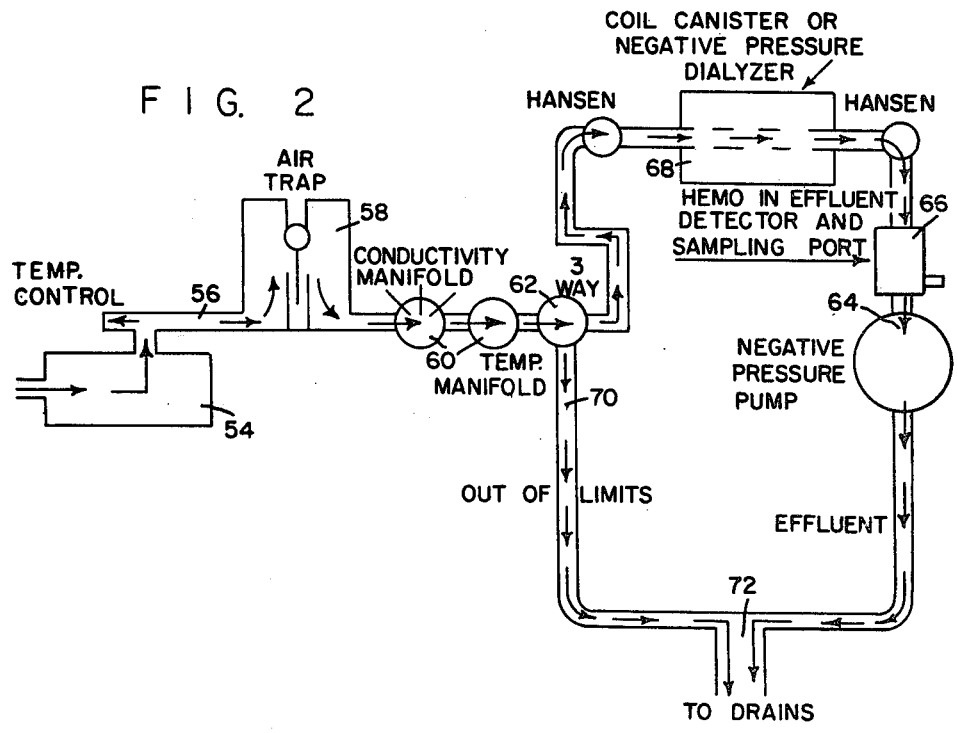

PRESSURE AND FLUID FLOW ACTIVATED, SIMPLIFIED PROPORTIONING SYSTEM

Continuation-in-part of Ser. No. 161,065 filed June 19, 1980 abandoned

BACKGROUND OF THE INVENTION

Hemodialysis has become the accepted therapy for "End Stage Renal Disease" (ESRD). Since the establishment of federal financing for all U.S. citizens, tens of thousands of terminal patients have been given a second chance to live by hospital and kidney center dialysis. Treatments average five hours in duration, and three times a week in frequency.

Public law changed the intent of the ESRD program in 1979 by directing that patients must be given the option of home-dialysis treatment. Emphasis on home dialysis promises to substantially reduce reimbursement costs by the federal agencies.

Hemodialysis equipment currently available is in general, large, heavy and not really suited for the home, much less for travel.

This invention relates to easily transported, compact and light weight equipment that sacrifices none of the reliability or efficiency of its larger counterparts. This equipment can be used with any commercially available dialyzer, whether "coil" or "flat plate" or "capillary". (The dialyzer is a semi-permeable membrane device that, together with other hemodialysis equipment, purifies the blood by osmotic differentials, and removes excess fluid by pressure differentials.)

Hemodialysis requires, first of all, a "proportioning" system which accurately dilutes the dialysate concentrates with water (usually 34:1), and homogeneously mixes the resulting solution. The "dialysate" module then heats and deaerates the solution, and controls the rate of flow to the dialyzer.

Hemodialysis systems employ a built-in conductivity meter to ensure accurate dilution of dialysate concentrate between critical limits. Conventional calibration is generally performed by comparing the reading of this instrument with an external instrument by passing the diluted dialysate concentrate through said external instrument (such as a laboratory asmometer). Another method is to employ a "check point" or "calibrate circuit" within the built-in conductivity meter, usually a resistor in the electronic circuit. These prior art calibration methods fail to afford complete reliability and patient safety because of inherent variables, including significant potential for human error.

This invention describes a novel, simplified compact system of accurate proportioning which eliminates the need for complex mechanisms and controls (often combinations of precision hydraulic piston pumps operated by water pressure), and for sophisticated electronic sensing and feed-back serve circuits.

SUMMARY OF THE INVENTION

A main pump runs continuously, pumping water from a supply source into a mix ("proportioning") tank and simultaneously into a concentrate metering pump, thereby propelling the metered concentrate into the mix tank. Alternately, the main pump delivers proportioned dialysate to the reservoir (storage) tank after each "batch" has been prepared.

As the proportioning tank fills, pressure therein increases until a preset level is reached (e.g., 25 psi). A pressure switch then applies electrical power to a pair of directional solenoid valves at the input and output of the pump. When energized, these direct the flow of proportioned dialysate from the proportioning tank to the reservoir tank. When they are de-energized, the flow is directed from the water source into the proportioning tank and concentrate pump.

An air-breathing check valve in the proportioning tank opens on demand to facilitate the emptying cycle.

When the emptying cycle is initiated, a flow switch (located between the proportioning tank and reservoir tank) is actuated, picks up the electrical load from the pressure switch, and continues to supply power to the directional solenoid valves until the proportioning tank empties and flow ceases. The pressure switch automatically resets for another fill cycle.

When the proportioning tank has been emptied and its contents have been delivered under pressure into the storage tank, the directional valves deenergize, returning to their original state, and another proportioning-mixing cycle begins. The frequency of this cycle is determined by the rate of delivery of proportioned dialysate to the kidney, and by the volumes of the proportioning and storage tanks, e.g., a 500 cc/min. output, and 500-cc mix-proportioning tanks, would cycle one a minute.

The system completely eliminates the need for sophisticated electrical control of relay logic and other elements.

The balance of the system includes:
- A flow meter and a flow controller.
- A conductivity-measuring system.
- A temperature-control and heating system.
- A three-way, fail-safe, solenoid-actuated directional valve. Normal mode to drain; energized mode to patient (when both conductivity and temperature system are "in limits").
- An air-removal system.
- A "sterilize" (disinfecting) mode in which heater, conductivity system, and three-way valve are deenergized. This system is interlocked with Hansen connectors to prevent unintentional operation in the "sterilize"mode.
- Display of temperature and conductivity, with controls for adjusting both parameters.
- For negative pressure dialyzers, a source of negative pressure, a control valve, and a pressure-indicating gauge.

BRIEF DESCRIPTION OF THE DRAWING

FIG. 1 is a diagram flow sheet of a part of the system, and

FIG. 2 is a diagram and flow sheet of the remainder of the system.

PREFERRED EMBODIMENT OF THE INVENTION

As an example, in FIG. 1, the reference 10 indicates a water supply under pressure controlled by a convenient valve 12 if such a supply is available. The reference 14 represents a water storage apparatus (no pressure) which may be used alternatively with respect to the water under pressure. The source 10 and 14 may be connected to flow into pipe 16 selectively by proper valving.

A directional three-way valve 18 receives the water from the pipe 16 passing it through pipe 20 to a gear pump 22. The gear pump 22 leads to a pipe 24 to another three-way valve 26 utilized to direct the water through pipe 28 and branch 30 and thence into the proportioning tank 32. Some of the water passes through a branch pipe 34 into a concentrate pump 36 which receives the concentrate from a concentrate source 38 through a pipe 40 and it will be seen that the concentrate and the water move together into the proportioning tank 32, becoming mixed.

When the proportioning tank is substantially full, the solution then moves back through pipe 30 and pipe 42 to the three-way valve 18, gear pump 22, three-way valve 26, pipe 44, through flow switch 46 and pipe 48 to a storage tank 50.

The pressure switch 52 operates the three-way valves in a desired sequence to carry out the operation described above. When the proportioning tank arrives at a certain predetermined high pressure, the pressure switch operates to actuate the three-way valves 18 and 26 so that pipes 28 and 34 are closed, and the proportioning operation ceases. The proportioned dialysate then proceeds through pipes 30, 42, etc., as above described, to the storage tank 50, ready for use. When the emptying cycle is initiated, the flow switch 46 actuates, assumes the electrical load from pressure switch 52, and continues to supply power to the directional solenoid valves 18 and 26 until the mix tank empties. The switches 46 and 52 automatically reset for another proportioning cycle.

From the storage tank 50, the proportioned dialysate proceeds to a heater 54, a temperature control 56, an air trap 58, a conductivity and temperature manifold 60, and a three-way valve 62 which is automatically operated by the conductivity and temperature monitors to pass the solution effectively through the artificial kidney 68. The effluent from the artificial kidney 68 passes through the blood-leak detector and sampling port 66 and finally to drain 72. Should concentration and/or temperature of proportioned dialysate be out-of-limits, the three-way valve 62 functions as a positive fail-safe by directing the dialysate through conduit 70 to drain 72. The pump 64 provides the negative pressure essential for operation of parallel-flow type dialyzers, and also for pumping of effluent to drain from coil-type dialyzers.

With reference to the criticality of proportioning of dialysate concentrate, this invention will directly check and calibrate the built-in conductivity meter with its built-in cell. Means is provided to introduce a *standard reference solution* into the cell and observe the meter reading as a means of directly calibrating the cell, its electrodes and its temperature compensation, as well as the electronics and the meter.

This invention affords a system which need not rely on external water supply pressure.

The invention can be used with a "pre-mix" dialysate.

The dialysate-proportioning system of this invention can be used as a source of dialysate supply for a multiple-patient hemodialysis unit.

We claim:

1. A proportioning system comprising a proportioning mixing tank, a storage tank, a source of concentrate, a source of diluent, a constantly acting pump means, and lines for directing the diluent from said source of diluent to the proportioning tank and from the proportioning tank to the storage tank, the pump means pumping concentrate through a conduit from said source of concentrate into the proportioning tank in a prearranged proportion of the concentrate and the diluent,
a first sensor operated pressure actuated switch means associated with the proportioning tank for actuation at a certain predetermined pressure in the proportioning tank as said proportioning tank fills, and a second sensor operated fluid flow switch means located in the line just prior to the storage tank for actuation at a predetermined fluid flow,
directional valve means in the lines between said pump means, the proportioning tank and the storage tank, said valve means being actuated first by said first sensor operated pressure actuated switch means for directing the fluid from the proportioning tank to the storage tank while said pump means is still operating, while said valve means shut off the proportioning tank from the concentrate and diluent, the second sensor operated fluid flow switch means being actuated to hold said valve means in this position as long as the flow exists continuing this state of said directional valve means, and said second sensor operated fluid flow switch means operating to reverse the directional valves to their original state to once more direct the diluent and concentrate to the proportioning tank.

2. The proportioning system of claim 1 wherein said valve means are three-way valves.

3. The system of claim 1 including a branch line, wherein said pump means delivering the diluent to the proportioning tank through the branch line also delivers the concentrate to the proportioning tank simultaneously.

4. The system of claim 1 including a branch line wherein said pump means delivering the diluent to the proportioning tank through the branch line also delivers the concentrate to the proportioning tank,
and a concentrate pump means maintaining the amount of concentrate in proportion to the amount of diluent pumped into the proportioning tank.

5. The system of claim 1 including means for providing that the diluent supply is unpressurized.

6. The system of claim 1 including means for providing that the diluent supply is under pressure.

7. The system of claim 1 wherein said pump means is a gear pump.

8. The proportioning system of claim 1 including means to supply a single patient.

9. The proportioning system of claim 1 including means to supply multiple patients.

10. The proportion system of claim 1 including negative pressure means for "plate" or "capillary" dialyzers.

11. The system of claim 1 including a conventional electronic conductivity test system which can be calibrated in place by introducing a standard solution into its integral measuring cell.

\* \* \* \* \*